(12) United States Patent
Burnside et al.

(10) Patent No.: US 6,793,934 B1
(45) Date of Patent: Sep. 21, 2004

(54) SOLID ORAL DOSAGE FORM

(75) Inventors: Beth A. Burnside, Silver Spring, MD (US); Henry Flanner, Montgomery Village, MD (US); Xiaodi Guo, Derwood, MD (US); Rong Kun Chang, Gaithersburg, MD (US)

(73) Assignee: Shire Laboratories, Inc., Rockville, MD (US)

( * ) Notice: Subject to any disclaimer, the term of this patent is extended or adjusted under 35 U.S.C. 154(b) by 0 days.

(21) Appl. No.: 09/457,248

(22) Filed: Dec. 8, 1999

(51) Int. Cl.$^7$ .................................................. A61K 9/20
(52) U.S. Cl. ................... 424/464; 424/451; 424/489; 424/400; 424/600; 424/682
(58) Field of Search .................. 424/451, 28.03, 424/489, 473, 400, 464, 600, 682

(56) References Cited

U.S. PATENT DOCUMENTS

| | | | |
|---|---|---|---|
| 5,075,291 A | 12/1991 | DuRoss | 514/60 |
| 5,182,103 A * | 1/1993 | Nakane et al. | 424/78.03 |
| 5,188,836 A | 2/1993 | Muhammad et al. | 424/431 |
| 5,585,115 A * | 12/1996 | Sherwood et al. | 424/489 |
| 5,800,834 A | 9/1998 | Spireas et al. | 424/451 |
| 6,280,770 B1 | 8/2001 | Pather et al. | 424/465 |
| 6,342,249 B1 * | 1/2002 | Wong et al. | 424/473 |

OTHER PUBLICATIONS

Spireas, et al., *Pharmaceutical Research*, vol. 9, No. 10, pp. 1351–1358 (1992).

Takami, et al., *Chem. Pharm. Bull.*, vol. 44, No. 4, pp. 868–870 (1996).

Spireas, et al., *J. Pharm. Sci.*, vol. 87, No. 7, pp. 867–872 (Jul. 1998).

* cited by examiner

Primary Examiner—Thurman K. Page
Assistant Examiner—Konata M. George
(74) Attorney, Agent, or Firm—M. Elisa Lane

(57) ABSTRACT

A pharmaceutical composition comprising a solid carrier containing a liquid selected from the group consisting of a liquid active agent, a liquid enhancer, or a combination thereof.

26 Claims, No Drawings

SOLID ORAL DOSAGE FORM

The present invention relates to solid oral dosage forms containing liquid ingredients, e.g., liquid active agent(s), liquid oral absorption enhancer(s) or liquid solvent(s) for selected drugs, and the processes to prepare them.

BACKGROUND OF THE INVENTION

It is very difficult to incorporate liquid materials, such as surfactants or oils, for example, polysorbates (Tween 20, 40, 60, 80), polyglycolized glycerides (Labrasol), and vegetable oil, etc., into a solid dosage form, especially a tablet dosage form. Most pharmaceutical carriers cannot carry liquids in the form of a free-flowing powder. When a carrier containing liquid is under load, the liquid will be squeezed out, leading to a reduced compactibility and compressibility of the carrier. Silicas and other ingredients such as microcrystalline cellulose, magnesium oxide, and maltodextrin, can carry liquids in the form of a free-flowing powder. See e.g. U.S. Pat. No. 5,800,834, but these powdered liquids have poor compressibility properties (Spireas, et al, *Journal Pharm. Sci.* 87 (7): 867 (1998); Spireas, et al, Pharmaceutical Research 4 (10): 1351 (1992); Shah et. al. Drug Development and Industrial Pharmacy 19 (13), 1587 (1993). Liquisolid technology overcomes the limitations of the powdered liquid to form tablets; however, it requires the use of a liquid carrier and a powder coating.

It is an object of the invention to obtain a pharmaceutical composition which comprises a liquid agent in the form of a free-flowing powder which can be encapsulated into hard gelatin capsules, incorporated into tablets or other solid delivery dosage forms.

SUMMARY OF THE INVENTION

The present invention relates to an immediate-release pharmaceutical composition comprising a liquid drug, drug solutions, oral absorption enhancer solution or liquid oral absorption enhancers in the form of a free-flowing powder. The free-flowing powders advantageously can be encapsulated into hard gelatin capsules, compressed into tablets, or incorporated into other dosage forms without the aid of a powder coating. Applicants have found that excipients that act as liquid carriers successfully absorb or carry liquid agents and can be compressed into a tablet formulation.

In accordance with an aspect of the present invention, there is provided a solid oral dosage form. The solid oral dosage form comprises a solid carrier containing a liquid. The solid carrier comprises a member selected from the group consisting of magnesium aluminometasilicate, dibasic calcium phosphate, or a combination thereof. The liquid comprises a member selected from the group consisting of a liquid pharmaceutically or biologically active drug or agent, a liquid enhancer, or a combination thereof. The oral dosage form further comprises a solid active a gent wherein the liquid does not include an active agent.

The term "liquid," as used herein, means a liquid at room temperature, or a material that becomes a liquid during processing, especially during a process that requires force or shear, and more specifically, one that forms a tablet.

The term "liquid active agent" includes a pharmaceutically or biologically active drug or agent as a liquid or dissolved or dispersed in a liquid.

In general, the liquid is present in the solid oral dosage form in an amount of at least 5 wt. %, preferably in an amount of at least 15 wt. %, based on the total weight of the solid oral dosage form. In general, the liquid is present in the solid oral dosage form in an amount which does not exceed 60 wt. %, and more preferably does not exceed 50 wt. %, and still more preferably does not exceed 35 wt. %.

It has further been found to be of particular advantage that due to the high oil adsorption capacity of these excipients, there is no need for an overcoating, such as silicon dioxide, on the formulation to maintain the free-flow and compression properties.

In one aspect of this invention, the oral dosage form includes absorption enhancers in combination with drugs of low bioavailability (less than approximately 30% bioavailablity). The liquid component may be a mixture with the drug or may be incorporated into a non-drug containing layer, say for example in a multilayer tablet, to minimize degradation caused by intimate contact of drug with the liquid agent.

In one embodiment of this aspect, the carrier of the invention can enhance advantageously the solubility of agents having low water solubility (less than 1.0 mg/ml), for example, corticosteroids which results in lower absorption. The common adverse effect of the long-term therapy of corticosteroids, such as prednisolone, prednisone, is osteoporosis. The use of the granulated dibasic calcium phosphate as a carrier and as a calcium source has significant benefits to minimize the side effect of osteoporosis and to enhance the efficacy of corticosteroids.

In another embodiment of this aspect, the carrier of the invention provides a faster absorption rate of the agent, thereby enhancing the efficacy and reducing or minimizing loss of the agent to pre-systemic metabolism.

In another aspect, the carrier of the invention advantageously can provide a synergistic effect of the active agent. For example, estrogen, especially β-estradiol, undergoes extensive first pass metabolism and requires fast drug input to saturate the enzyme in order to minimize pre-systemic metabolism. In a preferred embodiment of the present invention, the carrier comprising calcium has a synergistic effect on estrogen and it is more effective than estrogen alone at increasing bone mass of the hip and forearm. Thus, the application of liquisolid technology using the granulated dibasic calcium phosphate as a carrier and as a calcium source may increase the benefits of hormone replacement therapy.

In another aspect, the carrier of the present invention may act as a protective agent against gastric irritation caused by some drugs such as ibuprofen and naproxen. The magnesium aluminometasilicate acts as an antacid to provide some protection against the gastric irritation caused by such drugs, in addition to serving as a liquid carrier to achieve a faster absorption.

In a preferred embodiment the solid phase pharmaceutical formulations comprise the carrier spherically granulated dibasic calcium phosphate (Fujicalin, Fuji Chemical Industry Co., Ltd.), or, in an alternative embodiment, magnesium aluminometasilicate (Neusilin, Fuji Chemical Industry Co., Ltd.). Thus in one aspect of the invention these two excipients are used as a carrier for converting liquid drugs, drug solutions into free-flowing powders. For example, magnesium aluminometasilicate and granulated dibasic calcium phosphate may be used as a carrier for a liquid drug, e.g., benzonatate, to provide an alternative dosage form to soft gelatin capsules. In addition, using an antacid, e.g., magnesium aluminometasilicate, may minimize the side effects of gastrointestinal irritation caused by benzonatate.

In another embodiment of this aspect, the carrier can hold, in addition to the enhancers and drugs, agents that inhibit crystal formation.

Agents that inhibit crystal formation of the active pharmaceutical ingredients or absorption enhancers by complexation, surface coating, and/or physical blocking also can be incorporated into the formulation to prevent or slow the rate of crystal propagation. Examples of the agents that inhibit crystal growth of the active pharmaceutical ingredients or absorption enhancers include polyvinylpyrrolidone, polyethylene glycol, cyclodextrins, gelatin, maltodextrin, sorbitol, and polyglyceryl mixed vegetable fatty acid esters.

DETAILED DESCRIPTION OF THE INVENTION

The carrier of the present invention may be employed in preparing formulations for drugs which include, but are not limited to, valproic acid, benzonatate, simethicone, methylclothiazide, prednisolone, prednisone, ibuprofen, naproxen, aspirin, acetaminophen, dihydroergotamine mesylate, famotidine, omeprasole, chloropheniramine, ranitidine, diclofenac sodium, cimetidine, guaifenesin, glypizide, estradiol, acyclovir, ketoprofen, desmopressin and bupropion.

The powdered solution technology of the present invention utilizing the carrier for forming a liquid agent into a dry, non-adherent, free-flowing compressible powder can generally be employed when administration of an active agent in a liquid formulation would be disadvantageous. A powder can be considered free flowing if it meets the processing characteristics such that in the process of making tablets the resulting tablet weights are uniform or in the process of filling capsules, the resulting capsule weight is uniform. Such applications include, but are not limited to:
1) a liquid drug;
2) a liquid drug with a liquid oral absorption enhancer; liquid oral absorption enhancers can include, but are not limited to, polysorbate or Tween type surfactants, polyglycolized glyceride, such as Labrasol;
3) a liquid drug with a solid absorption enhancer; solid absorption enhancers can include Gelucire 44/14 which could be melted and absorbed onto the surface of the carrier, then used as a filler/powder during compression. (Gelucire cannot be compressed because it is thixotropic-it turns to liquid when under stress, but is otherwise solid);
4) a poorly water-soluble solid drug dissolved in a suitable nonvolatile solvent system;
5) a solid drug with poor bioavailability dissolved in a suitable nonvolatile solvent system;
6) a solid drug with poor bioavailability dissolved in a suitable nonvolatile solvent system containing an oral absorption enhancer, for example Nifedipine dissolved in triethyl citrate and labrasol as an enhancer;
7) a poorly water-soluble solid drug dispersed in a suitable nonvolatile solvent system;
8) a solid drug with absorption problems (less than 30% bioavailability) dispersed in a suitable nonvolatile solvent system;
9) a solid drug with poor bioavailability dispersed in a suitable nonvolatile solvent system containing an oral absorption enhancer;
10) a drug containing microemulsion, either an oil-in-water type or a water-in-oil type; the term microemulsion is used herein to mean an emulsion microemulation or other organized media, all of which consist generally of a surface active agent, a hydrophobic phase and a hydrophilic phase. They also can contain other optional ingredients such as buffers and cosurfactants, and the like;
11) a liquid absorption enhancer;
12) a liquid solubility enhancer.

The drug-containing liquids can be blended with either the granulated dibasic calcium phosphate or magnesium aluminometasilicate or in combination in a V-shaped blender to form a free-flowing, dry powder. The blending process also can be carried out in a planetary mixer, high shear granulator, fluid-bed granulator, or by a simple mixing using a spatter or other mixing methods known to one skilled in the art. Subsequently, the resulting powdered solution can be further blended with other pharmaceutical processing aids, such as bulking agent, disintegrant, glidant, and lubricant, then compressed into tablets on a rotary press using appropriate tooling.

In addition, the powdered solution can be granulated with a binding solution to enlarge the particle size for further processing. The wet granules are dried in an oven or fluidized-bed. The dried granules are sieved through a suitable sieve screen to obtain the desired particle size. The resulting granules can be blended with other processing aids and compressed into tablets or encapsulated into capsules. Customary additional processing known to one skilled in the art can take place to the granules, tablets or capsules.

The bulking agent can be microcrystalline cellulose, mannitol, xylitol, starches and the like. Disintegrants can be starches, crospovidone, sodium starch glycolate, croscarmellose sodium and the like. Antiadherents and glidants can be talc, corn starch, silicon dioxide, sodium lauryl sulfate, metallic stearates and the like. Lubricants can be magnesium stearate, calcium stearate, sodium stearate, stearic acid, sterotex, talc, waxes and the like. Binding agents can be polyvinylpyrrolidone, starch, methylcellulose, hydroxypropyl methycellulose, carboxy methyl cellulose, etc. Oral absorption enhancers can include, but are not limited to, the following: polysorbates, sorbitan esters, poloxamer block copolymers, PEG-35 castor oil, PEG-40 hydrogenated castor oil, caprylocaproyl macrogol-8 glycerides, PEG-8 caprylic/capric glycerides, sodium lauryl sulfate, dioctyl sulfosuccinate, polyethylene lauryl ether, ethoxydiglycol, propylene glycol mono-di-caprylate, glycerol monocaprylate, glyceryl fatty acids ($C_8$–$C_{18}$) ethoxylated, oleic acid, linoleic acid, glyceryl caprylate/caprate, glyceryl monooleate, glyceryl monolaurate, caprylic/capric triglycerides, ethoxylated nonylphenols, PEG-(8–50) stearates, olive oil PEG-6 esters, triolein PEG-6 esters, lecithin, d-alpha tocopheryl polyethylene glycol 1,000 succinate, citric acid, and sodium citrate. In addition, a combination of oral absorption enhancers can be used to improve the absorption further. The nonvolatile solvents can include, but are not limited to, the following: polyethylene glycol, propylene glycol, glycerin, vegetable oil, cotton seed oil, peanut oil, sesame oil, mineral oil, glycofurol, propylene glycol dicaprylate/dicaprate, glyceryl caprylate/caprate, oleic acid, polysorbates, sorbitan esters, caprylocaproyl macrogol-8 glycerides, ethoxydiglycol, and poloxamer block copolymers. Furthermore, cosolvency can be used to enhance the solubility of drugs in the mixed solvent system.

EXAMPLES

Magnesium aluminometasilicate (Neusilin, Fuji Chemical Industry Co., LTD), granulated dibasic calcium phosphate (Fujicalin, Fuji Chemical Industry Co., LTD), Magnesium stearate (Mallincrodt), croscarmellose sodium (Ac-di-sol, FMC corp.), silicon dioxide (Cabosil, Cabot Corp.), caprylocaproyl macrogol-8 glycerides (Labrasol, Gattefosse), oleoyl macrogol-6 glycerides (Labrafil, Gattefosse).

The procedures described below are performed under ambient conditions. The mixing step can be achieved by using a V-shaped blender, a double cone blender, a planetary blender, or a high shear blender. The mixing time for liquid ingredients and lubricant were 10 minutes and 5 minutes, respectively; however, the mixing time for liquid can be varied from 5 minutes to 45 minutes with no apparent adverse effect. The Stokes rotary tablet press was used to compress the powder blend into tablets. Other rotary tablet presses, such as Kikusui press, Hata press, etc. also can be used. The batch size for the examples provided herein is around 2 kg. The batch size can be scaled up with no difficulty.

Example 1

| Ingredient | Composition (%) | mg/Tablet |
| --- | --- | --- |
| Benzonatate | 20.0 | 100 |
| Magnesium aluminometasilicate | 60.0 | 300 |
| Granulated dibasic calcium phosphate | 19.0 | 95 |
| Magnesium stearate | 1.0 | 5 |

Ethyl alcohol (20% based upon the weight of benzonatate) is added into benzonatate to reduce the viscosity and to facilitate the blending. Magnesium aluminometasilicate and granulated dibasic calcium phosphate are blended in a suitable V-shaped blender. The prepared benzonatate is added to the blender and mixed. The ethyl alcohol is removed from the powder blend in an oven. The powdered solution is blended with magnesium stearate. The lubricated powder blend is compressed into tablets.

Example 2

| Ingredient | Composition (%) | mg/Tablet |
| --- | --- | --- |
| Simethicone | 16.7 | 50 |
| Magnesium aluminometasilicate | 82.3 | 247 |
| Magnesium stearate | 1.0 | 3 |

Ethyl alcohol (20% based upon the weight of simethicone) is added into simethicone to reduce the viscosity and to facilitate the blending. The simethicone is added to magnesium aluminometasilicate in a suitable V-shaped blender and mixed. The ethyl alcohol is removed from the powder blend in an oven. The powdered solution is blended with magnesium stearate. The lubricated powder blend is compressed into tablets.

Example 3

| Ingredient | Composition (%) | mg/Tablet |
| --- | --- | --- |
| Estradiol | 0.2 | 1 |
| Propylene glycol | 10.0 | 50 |
| Magnesium aluminometasilicate | 3.8 | 19 |
| Granulated dibasic calcium phosphate | 80.0 | 400 |
| Croscarmellose sodium | 5.0 | 25 |
| Magnesium stearate | 1.0 | 5 |

Estradiol is dissolved in propylene glycol. Magnesium aluminometasilicate, granulated dibasic calcium phosphate, and croscarmellose sodium are blended in a suitable blender. The estradiol solution is added to the powder blend and blended. Magnesium stearate is added to the powder and blended. The lubricated powder blend is compressed into tablets.

Example 4

| Ingredient | Composition (%) | mg/Tablet |
| --- | --- | --- |
| Prednisolone | 1.0 | 5 |
| Propylene glycol | 12.0 | 60 |
| Granulated dibasic calcium phosphate | 80.0 | 400 |
| Croscarmellose sodium | 5.0 | 25 |
| Silicon Dioxide | 1.0 | 5 |
| Magnesium stearate | 1.0 | 5 |

Prednisolone is dispersed and pulverized in propylene glycol using a homogenizer. The granulated dibasic calcium phosphate and croscarmellose sodium are blended in a suitable blender. The prednisolone dispersion is added to the powder blend and mixed. Silicon dioxide is added to the powders and blended. Magnesium stearate is added to the powders and blended. The lubricated powder blend is compressed into tablets.

Example 5

| Ingredient | Composition (%) | mg/Tablet |
| --- | --- | --- |
| Dihydroergotamine mesylate | 0.2 | 1.00 |
| Labrasol | 6.11 | 30.56 |
| Labrafil | 1.52 | 7.60 |
| Oleic acid | 0.74 | 3.68 |
| Water | 7.6 | 38.16 |
| Granulated dibasic calcium phosphate | 80.0 | 400.00 |
| Croscarmellose sodium | 2.8 | 14.00 |
| Magnesium stearate | 1.0 | 5.00 |

Dihydroergotamine mesylate, Labrasol, Labrafil, oleic acid, and water are mixed to form a microemulsion. The microemulsion is added to granulated dibasic calcium phosphate and croscarmellose sodium in a V-shaped blender. Magnesium stearate is added to the powders. The powder blend is compressed into tablets.

Example 6

Glipizide Free Flowing Powder

A 1:1 weight ratio of Neusilin and Tween 80 are mixed. Glipizide is then added to a tablet formulation and compressed. Alternatively, the glipizide is dispersed in the Tween 80, and the mixture is absorbed onto the Neusilin. The powder can then be compressed into a tablet. Analysis of the powder made by either method results in the same solubility enhancement of glipizide. The flexibility in the manufacturing method gives the formulator the option to prepare a free flowing powder by the method that best suits the formulation situation. For example if no dispersion equipment were available, liquid/powder blending would be suitable in a standard low shear granulator (planetary mixer) or a suitable high shear mixer. If the drug were particularly hazardous, the drug could be dispersed in a solubilizer, then blended with the carrier to form a safe free flowing powder.

Example 7

| Ingredient | Composition (%) | mg/Tablet |
|---|---|---|
| Valproic acid | 16.7 | 125 |
| Isopropyl alcohol | — | 50 |
| Granulated dibasic calcium phosphate | 46.0 | 345 |
| Croscarmellose sodium | 3.2 | 24 |
| Magnesium aluminometasilicate | 33.3 | 250 |
| Magnesium stearate | 0.8 | 6 |

Valproic acid is mixed with isopropyl alcohol. The granulated dibasic calcium phosphate, magnesium aluminometasilicate, and croscarmellose sodium are blended in a suitable mixer, e.g., high shear mixer or planetary mixer. The valproic acid liquid is added to the powder blend and mixed. The isopropyl alcohol is dried off using an oven or a fluidized dryer. The dried material is screened through a 30 mesh or other suitable screen. Magnesium stearate is added to the powders and blended. The lubricated powder blend is compressed into tablets.

Example 8

| Ingredient | Composition (%) | mg/Tablet |
|---|---|---|
| Glipizide | 2.5 | 10.00 |
| Tween 80 | 12.5 | 50.00 |
| Magnesium aluminometasilicate | 84.0 | 336.00 |
| Magnesium stearate | 1.0 | 4.00 |
| Surelease | 4.0 | 16.00 |
| Opadry white | 2.0 | 8.00 |

Tween 80 is mixed with magnesium aluminometasilicate. Glipizide is blended with the powder mix. Magnesium stearate is blended with the powder blend. The lubricated powder blend is compressed into tablets. The core tablets are film coated with Surelease and overcoated with Opadry white.

Example 9

| Ingredient | Composition (%) | mg/Tablet |
|---|---|---|
| Calcitrol, 0.0005% | — | — |
| Ethanol, 10% | — | — |
| Granulated dibasic calcium phosphate | 95.0 | 399 |
| Croscarmellose sodium | 4.0 | 16.8 |
| Magnesium stearate | 1.0 | 4.2 |

The calcitrol is dissolved in the ethanol, and the resulting solution is added to the granulated dibasic calcium phosphate, and blended. The ethanol then is removed from the powder blend in an oven. The powder blend then is blended with the croscarmellose sodium and magnesium stearate. The lubricated powder blend then is compressed into tablets.

Although magnesium aluminometasilicate and/or dibasic calcium phosphate are preferred for incorporating a liquid into a sold oral dosage form, it is possible to use other solids; e.g., a solid that is capable of absorbing liquid in an amount that is at least 25% by weight and still maintain free-flowing and compressible properties.

It is to be understood, however, that the scope of the present invention is not to be limited to the specific embodiments described above. The invention may be practiced other than as particularly described and still be within the scope of the accompanying claims.

What is claimed is:

1. A solid oral pharmaceutical dosage form, consisting of:
   (a) a solid carrier selected from magnesium aluminometasilicate, dibasic calcium phosphate, or both, which carrier contains an active agent or a liquid having one or more components selected from the group consisting of active agents, oral absorption enhancers, and solubility enhancers, and
   (b) pharmaceutical processing aids selected from one or more glidants, disintegrants, lubricants, and/or bulking agents,
   wherein said liquid-containing solid carrier is a free-flowing powder, and wherein said form is a tablet, capsule, or powder.

2. The solid oral pharmaceutical dosage form of claim 1, wherein the solid carrier contains an active agent, and wherein the liquid does not comprise an active agent.

3. The solid oral pharmaceutical dosage form of claim 1, wherein said solid carrier contains a liquid enhancer, and a solid active agent.

4. The solid oral pharmaceutical dosage form of claim 1, wherein said solid carrier contains a solid absorption enhancer, and said liquid contains an active agent.

5. The solid oral pharmaceutical dosage form of claim 1, wherein the active agent is a poorly water-soluble solid drug that is dissolved or dispersed in a solubility enhancer.

6. The solid oral pharmaceutical dosage form of claim 1, wherein the active agent is a poorly water-soluble solid drug that is dissolved or dispersed in a solubility enhancer.

7. The solid oral pharmaceutical dosage form of claim 1, wherein the active agent is a solid drug with poor bioavailability that is dissolved or dispersed in an absorption enhancer.

8. The solid oral pharmaceutical dosage form of claim 1, wherein the active agent is contained in a microemulsion.

9. The solid oral pharmaceutical dosage form of claim 1, wherein the oral absorption enhancer is one or more compounds selected from the group consisting of polysorbates, Tween surfactants, polyglycolized glycerides, sorbitan esters, poloxamer block copolymers, PEG-35 castor oil, PEG-40 hydrogenated castor oil, caprylocaproyl macrogol-8 glycerides, PEG-8 caprylic/capric glycerides, sodium lauryl sulfate, dioctylsulfosuccinate, polyethylene lauryl ether, ethoxydiglycol, propylene glycol mono-di-caprylate, glycerol monocaprylate, glycerol fatty acids ($C_8$–$C_{18}$) ethoxylated, oleic acid, linoleic acid, glyceryl caprylate/caprate, glyceryl monooleate, glyceryl monolaurate, caprylic/capric triglycerides, ethoxylated nonylphenols, PEG-(8-50) stearates, olive oil PEG-6 esters, triolein PEG-6 esters, lecithin, d-alpha tocopheryl polyethylene glycol 1,000 succinate, citric acid, sodium citrate, and Gelucire 44/14.

10. The solid oral pharmaceutical dosage form of claim 1, wherein the solid carrier is magnesium aluminometasilicate.

11. The solid oral pharmaceutical dosage form of claim 1, wherein the solid carrier is dibasic calcium phosphate.

12. The solid oral pharmaceutical dosage form of claim 1, which contains a combination of magnesium aluminometasilicate and dibasic calcium phosphate together with the active agent benzonatate dissolved in ethyl alcohol.

13. The solid oral pharmaceutical dosage form of claim 12, wherein the ethyl alcohol is evaporated after blending the active agent with the solid carrier.

14. The solid oral pharmaceutical dosage form of claim 1, which contains magnesium aluminometasilicate together with the active agent simethicone dissolved in ethyl alcohol.

15. The solid oral pharmaceutical dosage form of claim 14, wherein the ethyl alcohol is evaporated after blending the simethicone with the solid carrier.

16. The solid oral pharmaceutical dosage form of claim 1, which contains magnesium aluminometasilicate, dibasic calcium phosphate, and the active agent estradiol dissolved in propylene glycol.

17. The solid oral pharmaceutical dosage form of claim 1, which contains dibasic calcium phosphate together with the active agent prednisolone dissolved in propylene glycol.

18. The solid oral pharmaceutical dosage form of claim 1, which contains dibasic calcium phosphate together with a microemulsion of the active agent dihydroergotamine mesylate.

19. The solid oral pharmaceutical dosage form of claim 1, which contains magnesium aluminometasilicate and dibasic calcium phosphate together with the active agent valproic acid dissolved in isopropyl alcohol.

20. The solid oral pharmaceutical dosage form of claim 1, which contains magnesium aluminometasilicate together with the active agent glipizide and the oral absorption enhancer, Tween 80.

21. The solid oral pharmaceutical dosage form of claim 1, which contains dibasic calcium phosphate and the active agent Calcitrol dissolved in ethanol.

22. The solid oral pharmaceutical dosage form of claim 21, wherein the ethanol is evaporated after blending the active agent with the solid carrier.

23. The solid oral pharmaceutical dosage form of claim 1, wherein the amount of liquid present is at least 5 wt %.

24. The solid oral pharmaceutical dosage form of claim 1, wherein the amount of liquid present is at least 15 wt %.

25. The solid oral pharmaceutical dosage form of claim 4, wherein the solid absorption enhancer is Gelucire 44/14.

26. The solid oral pharmaceutical dosage form of claim 1, wherein the active agent is valproic acid, benzonate, simethicone, methylclothiazide, prednisolone, prednisone, ibuprofen, naproxen, aspirin, acetominophen, dihydroergotamine, mesylate, famotidine, omeprasole, chloropheniramine, ranitidine, diclofenac sodium, cimetidine, guaifenesin, glypicide, estradiol, acyclovir, ketoprofen, desmopressin and bupropion.

* * * * *

US006793934C1

(12) EX PARTE REEXAMINATION CERTIFICATE (6706th)
United States Patent
Burnside et al.

(10) Number: US 6,793,934 C1
(45) Certificate Issued: Mar. 17, 2009

(54) SOLID ORAL DOSAGE FORM

(75) Inventors: Beth A. Burnside, Silver Spring, MD (US); Henry Flanner, Montgomery Village, MD (US); Xiaodi Guo, Derwood, MD (US); Rong Kun Chang, Gaithersburg, MD (US)

(73) Assignee: Supernus Pharmaceuticals, Inc, Rockville, MD (US)

Reexamination Request:
No. 90/008,085, Jul. 3, 2006

Reexamination Certificate for:
Patent No.: 6,793,934
Issued: Sep. 21, 2004
Appl. No.: 09/457,248
Filed: Dec. 8, 1999

(51) Int. Cl.
*A61K 9/20* (2006.01)
*A61K 9/14* (2006.01)

(52) U.S. Cl. .................. 424/464; 424/400; 424/451; 424/489; 424/600; 424/682

(58) Field of Classification Search .................. None
See application file for complete search history.

(56) References Cited

U.S. PATENT DOCUMENTS

| 5,486,365 | A  | 1/1996 | Takado et al. |
| 6,103,260 | A  | 8/2000 | Luber et al. |
| 7,067,154 | B1 | 6/2006 | Valleri et al. |

FOREIGN PATENT DOCUMENTS

| EP | 0 001 247    | 4/1979  |
| EP | 0 448 091    | 9/1991  |
| JP | 58126808 A   | 7/1983  |
| JP | 62-81309     | 4/1987  |
| JP | 63-119426    | 5/1988  |
| JP | 63-198620    | 8/1988  |
| JP | 5-271066     | 10/1993 |
| JP | 8-301763     | 11/1996 |

OTHER PUBLICATIONS www.fujichemical.co.jp/English/neusilin/html.*
Corswant et al. "Triglyceride–Based Microemulsion for Intravenous Adminstration of Sparingly Soluble Substances," Journal of Pharmaceutical Sciences, vol. 87, No. 2, pp. 200–208, Feb. 1998.*
The Merck Index, Eleventh Edition, Merck & Co., Inc., Rahway, NJ 1989, pp. 171, 249, 256, 583, 594, 696, 1223, 1247, 1351, and 1559.*
The 4$^{th}$ Scientific Symposium on Drug Additives; Special Issue: Dissolution of Solid Preparation and Additives, by Yoshiharu Horita of Fuji Chemical Industry Co., Ltd., Feb. 1999, Tokyo, Japan, pp. 1–14 plus covers, in both English and Japanese.
Neusilin UFL2, Fuji Chemical Industry Co., Ltd., Tokyo, Japan, 1997.

* cited by examiner

*Primary Examiner*—Gary L Kunz

(57) ABSTRACT

A pharmaceutical composition comprising a solid carrier containing a liquid selected from the group consisting of a liquid active agent, a liquid enhancer, or a combination thereof.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–3, 5–8, 13 and 15–22 are cancelled.

Claims 4, 9–12, 14, 23–24 and 26 are determined to be patentable as amended.

Claim 25, dependent on an amended claim, is determined to be patentable.

4. [The solid oral pharmaceutical dosage form of claim 1,] *A solid oral pharmaceutical dosage form, consisting of:*
   (a) *a solid carrier selected from magnesium aluminometasilicate, dibasic calcium phosphate, or both,* wherein said solid carrier contains a solid absorption enhancer, and [said] *a* liquid [contains an] active agent, *and*
   (b) *pharmaceutical processing aids selected from one or more glidants, disintegrants, lubricants, and/or bulking agents,*
   wherein said liquid-containing solid carrier is a free-flowing powder, *and wherein said form is a tablet, capsule, or powder.*

9. The solid oral pharmaceutical dosage form of claim [1] *4*, wherein the [oral] *solid* absorption enhancer is one or more compounds selected from the group consisting of [polysorbates, Tween surfactants, polyglycolized glycerides, sorbitan esters,] poloxamer block copolymers, [PEG-35 castor oil, PEG-40 hydrogenated castor oil, caprylocaproyl macrogol-8 glycerides, PEG-8 caprylic/capric glycerides,] sodium lauryl sulfate, dioctylsulfosuccinate, [polyethylene lauryl ether, ethoxydiglycol, propylene glycol mono-dicaprylate, glycerol monocaprylate, glycerol fatty acids ($C_8$-$C_{18}$) ethoxylated, oleic acid, linoleic acid, glyceryl caprylate/caprate, glyceryl monooleate, glyceryl monolaurate, caprylic/capric triglycerides, ethoxylated nonylphenols, PEG-(8-50) stearates, olive oil PEG-6 esters, triolein PEG-6 esters,] lecithin, d-alpha tocopheryl polyethylene glycol [1,000 succinate], citric acid, sodium citrate, and Gelucire 44/14.

10. The solid oral pharmaceutical dosage form of claim [1] *4*, wherein the solid carrier is magnesium aluminometasilicate.

11. The solid oral pharmaceutical dosage form of claim [1] *4*, wherein the solid carrier is dibasic calcium phosphate.

12. The solid oral pharmaceutical dosage form of claim [1] *4*, which contains a combination of magnesium aluminometasilicate and dibasic calcium phosphate [together with the active agent benzonatate dissolved in ethyl alcohol].

14. The solid oral pharmaceutical dosage form of claim [1] *4*, which contains magnesium aluminometsilicate together with the active agent simethicone [dissolved in ethyl alcohol].

23. The solid oral pharmaceutical dosage form of claim [1] *4*, wherein the amount of liquid present is at least 5 wt %.

24. The solid oral pharmaceutical dosage form of claim [1] *4*, wherein the amount of liquid present is at least 15 wt %.

26. The solid oral pharmaceutical dosage form of claim [1] *4*, wherein the active agent is valproic acid, [benzonate] *benzonatate, and* simethicone[,methylclothiazide, prednisolone, prednisone, ibuprofen, naproxen, aspirin, acetominophen, dihydroergotamine, mesylate, famotidine, omeprasole, chloropheniramine, ranitidine, diclofenac sodium, cimetidine, guaifenesin, glypicide, estradiol, acyclovir, ketoprofen, desmopressin and bupropion].

* * * * *